(12) United States Patent
Hackett, Jr.

(10) Patent No.: US 6,688,160 B2
(45) Date of Patent: Feb. 10, 2004

(54) BARRIER TEST APPARATUS AND METHOD

(75) Inventor: Earl Thomas Hackett, Jr., Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/371,302

(22) Filed: Feb. 21, 2003

(65) Prior Publication Data

US 2003/0150255 A1 Aug. 14, 2003

Related U.S. Application Data

(63) Continuation-in-part of application No. 09/498,007, filed on Feb. 4, 2000, now Pat. No. 6,532,797.

(51) Int. Cl.[7] .............................................. G01N 15/08
(52) U.S. Cl. ......................................................... 73/38
(58) Field of Search ...................... 73/38, 28.01; 96/413

(56) References Cited

U.S. PATENT DOCUMENTS

| | | | | |
|---|---|---|---|---|
| 5,817,924 A | * | 10/1998 | Tuomela et al. ................ | 73/38 |
| 5,939,617 A | * | 8/1999 | Lim et al. ....................... | 73/38 |
| 6,532,797 B1 | * | 3/2003 | Hackett, Jr. .................... | 73/38 |

* cited by examiner

*Primary Examiner*—Robert Raevis

(57) ABSTRACT

An apparatus and method for measuring the barrier properties of porous materials particularly at low flow rates through the porous materials with the capability to separate flow through a test sample from flow through a particle counting means. The invention approximates real world situations and provides significant advantages in time and cost, especially in medical applications.

2 Claims, 5 Drawing Sheets

BARRIER TEST APPARATUS AND METHOD

CROSS REFERENCE TO RELATED APPLICATIONS

This is a continuation-in-part application of U.S. patent application Ser. No. 09/498,007 filed Feb. 4, 2000 now U.S. Pat. No. 6,532,797 and for which a Notice of Allowance was mailed Oct. 25, 2002.

BACKGROUND OF THE INVENTION

1. Field of the Invention

This invention relates to an apparatus and method for measuring the barrier properties of porous materials at various flow rates of particulates through the porous materials.

2. Description of the Related Act

Certain materials can be used for their barrier properties and the use may vary depending on how much of a barrier the material is intended to be. For example, filters are designed to restrict the passage of certain sized particles or particle-like matter. Other materials, such as packaging for sterilized articles, for example, would be designed to preclude the entrance of very small particles, such as microbial agents or any other substance that could compromise the sterility of what is enclosed in the package. Further, it may be desirable in some situations to allow a substance, water vapor, for example, to readily pass through a material that acts as a barrier to another substance.

It is therefore helpful to have some means for determining the barrier properties of materials. Methylene blue particulate penetration test, sodium chloride particulate penetration test and TSI 8130 automated filter tester are examples of systems used to test barrier performance or filter efficiency. These systems are usually based on drawing an air dispersion of particles at a fixed flow rate across a test sample. The flow rates tend to be relatively high because they are typically directed to ventilation applications where the volumes are very high and the medium to be tested is relatively porous, such as furnace filters. In these systems the rate of flow is typically set by the flow specification of the particle counter or detector. As such, one of the major limitations of these systems is the inability to separate the flow through the detector from the flow through the material being tested.

Another disadvantage of conventional testing methods, as previously noted, is that the materials are tested by drawing a dispersion of particles at a fixed flow rate. Because materials that have very high barrier properties (i.e., decreased porosity) produce very high pressure differentials, low face velocities can only be achieved by using unacceptably large sample sizes. Face velocity is the speed of the airflow through a material normalized for the sample size. A conventional test for barrier properties is presented in ASTM F1608-95 "Standard Test Method for Microbial Ranking of Porous Packaging Materials (Exposure Chamber Method)". In this method, the face velocity is about 21 cm/sec.

It is especially important to have alternate methods for determining the barrier properties of materials used in medical packaging, because testing in that area presents some especially difficult problems. Specialized equipment and procedures are required because biological agents are typically used as the challenge particles (i.e., the particles that are introduced to the material to test its barrier properties). These test methods with biological agents can typically operate at low flow rates however, a long time is required to grow and manually count the bacterial colonies, which makes the procedure expensive. As such, relatively few materials have been appropriately tested. A conventional method of testing using microbial agents is described in "A Discriminating Method for Measuring the Microbial Barrier Performance of Medical Packaging Papers", C. S. Sinclair and A. Tallentire, Medical Device & Diagnostic Industry 18(5) 228–241, 1996.

Therefore, a need exists for a relatively fast, relatively inexpensive apparatus and method for testing barrier properties of materials at various flow rates and without the necessity of using biological agents.

SUMMARY OF THE INVENTION

This invention includes a method for measuring barrier properties of a material comprising the steps of:

a) positioning a sample of the material in a holding means comprising a chamber wherein the material divides the chamber into a first portion and a second portion;

b) providing micrometer-sized particles;

c) generating a gas for mixing with the particles;

d) mixing the gas and the particles;

e) introducing the mixture of the particles and the gas into the first portion and wherein some percentage of the particles pass through the sample from the first portion to the second portion;

f) extracting from the first portion a small amount of the mixture that does not pass through the sample, g) counting the aerosol particles from f) in a particle counter, h) introducing a second gas through a predetermined-sized orifice into the second portion to sweep up particles that have passed through the sample;

i) extracting from the second portion the mixture that passed through the sample, j) counting the aerosol particles from i) in the particle counter, k) comparing the number of particles from g) to the number of particles from j).

This invention also includes an apparatus for measuring barrier properties of a material comprising:

a particle atomizer;

means for providing a gas, means for mixing the particles and the gas;

means for transporting the gas and particle mixture;

a sample holder comprising a chamber for positioning the sample wherein the sample divides the chamber into a first portion and a second portion, the first portion having an inlet and at least one outlet, and the second portion having an inlet and at least one outlet means for introducing a gas into the first portion through the first inlet means for introducing a gas into the second portion through the second inlet, and wherein the mixture from the receiving means enters the first portion through the first inlet and a first percentage of the aerosol particles exits the first portion through the first outlet into a counting means and a second percentage of the mixture passes through the material into the second portion and exits the second portion through the second outlet into the counting means, and means for comparing the particles form the first portion to the number of particles from the second portion.

DETAILED DESCRIPTION OF THE INVENTION

In order to evaluate the barrier performance of various materials, a device and accompanying procedures have been developed that evaluate barrier properties inexpensively and in a matter of minutes. The subject method and apparatus allow for rapid gathering of data and particularly:

an accurate measure of particle penetration at low flow rates (i.e., approaching zero), an accurate assessment of the most penetrating particle size at a given flow rate, and an accurate assessment of the flow rate at which a specific particle size has the maximum penetration.

The subject invention is particularly effective at flow rates less than 1 liter/minute (l/min) and even for flow rates approaching zero. The invention effectively parallels the ability of microbial testing methods to test at low flow rates, but in a much shorter time and is a significantly less cumbersome procedure.

A feature of the invention not found in conventional systems is the ability to separate flow through the sample material from flow to the counter and to allow measurement of barrier properties when flow rates approach zero. In tests of this type it is well known that some given quantity of challenge particles is introduced to one surface of a sample material and the number of challenge particles that pass through the sample is counted and compared to the amount of particles that were introduced. This difference in the number of particles represents the barrier property of the test material.

As was noted above, most conventional test devices are of limited value at low flow rates; i.e., less than about 1 l/min. Also, at low flow rates a conventional apparatus would require a long time (hours or, in some cases, days) to provide any meaningful data. However, such low flow rates are typical of what is encountered in real world situations.

Figure 1:
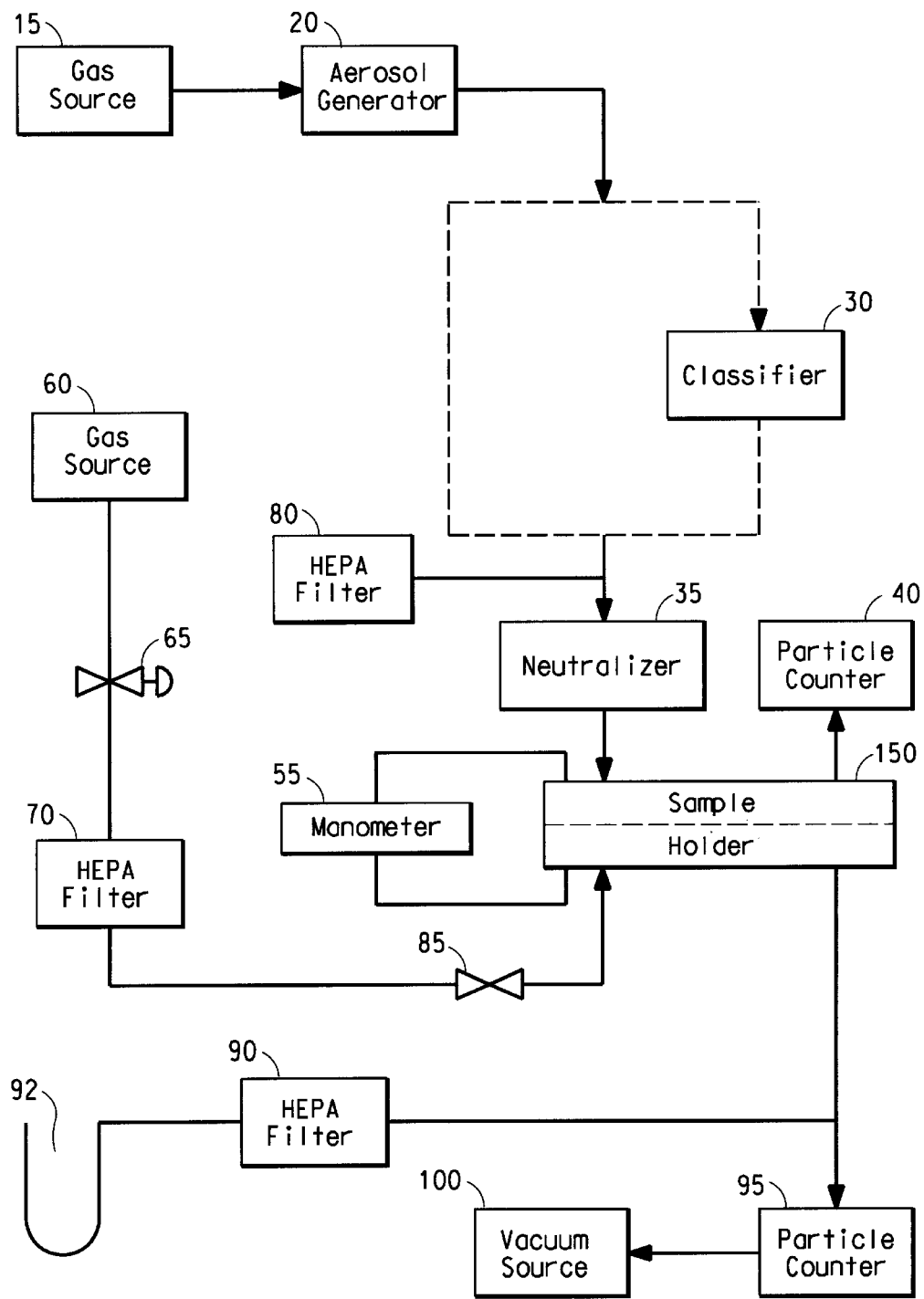
FIG. 1 is a schematic representation of the claimed apparatus.

The apparatus is depicted generally in FIG. 1 and described as follows. In the subject invention a generator 20 produces aerosol particles, specifically in the form of particularly-sized droplets of an appropriate oil such as dioctyl phthalate or dioctyl sebacate. The generator used herein is a TSI Model 3475 Condensation Aerosol Generator available from TSI Inc., St. Paul, Minn. Most of the other components are also available from TSI. The generator can produce particle sizes in the range from about 0.03 to about 6 micrometers. The aerosol particles are initially carried through the apparatus by a gas from a source 15. Preferably, the gas used is nitrogen. For the sake of convenience, the combination of the particles and the gas is typically referred to as particles. The combination of the particles and gas may be also referred to hereafter as a mixture. Depending on the size of the droplets, they may be directed to either of two different routes. Particle sizes in the size range of about 0.03 to 1 micrometer tend to be polydisperse, i.e., the particles vary in size. Those particles are passed through a classifier 30 so that only monodisperse aerosol particles are used. Monodisperse means that the particles are essentially the same size. When passed through classifier 30, the relatively small particles pick up a charge and therefore must be passed through a neutralizer 35 to remove the charge. Particles in the size range of 1–2 micrometers are typically not used because it is difficult to generate them in sufficient amounts to satisfy the speed requirements of the method. Generated particles in the range of about 2 to 6 micrometers are typically monodisperse and do not need to be passed through classifier 30. The larger particles tend to be monodisperse so it is unnecessary for them to pass through the classifier. However, for the sake of convenience, the large particles also pass through the neutralizer.

All of the parts of the apparatus are commercially available except the sample holder 150, which is more fully described below. The sample holder may be made from a conductive material, typically commercially available sheet metal. There are various areas where seals are present and, as such, numerous o-rings are used.

Figure 2:
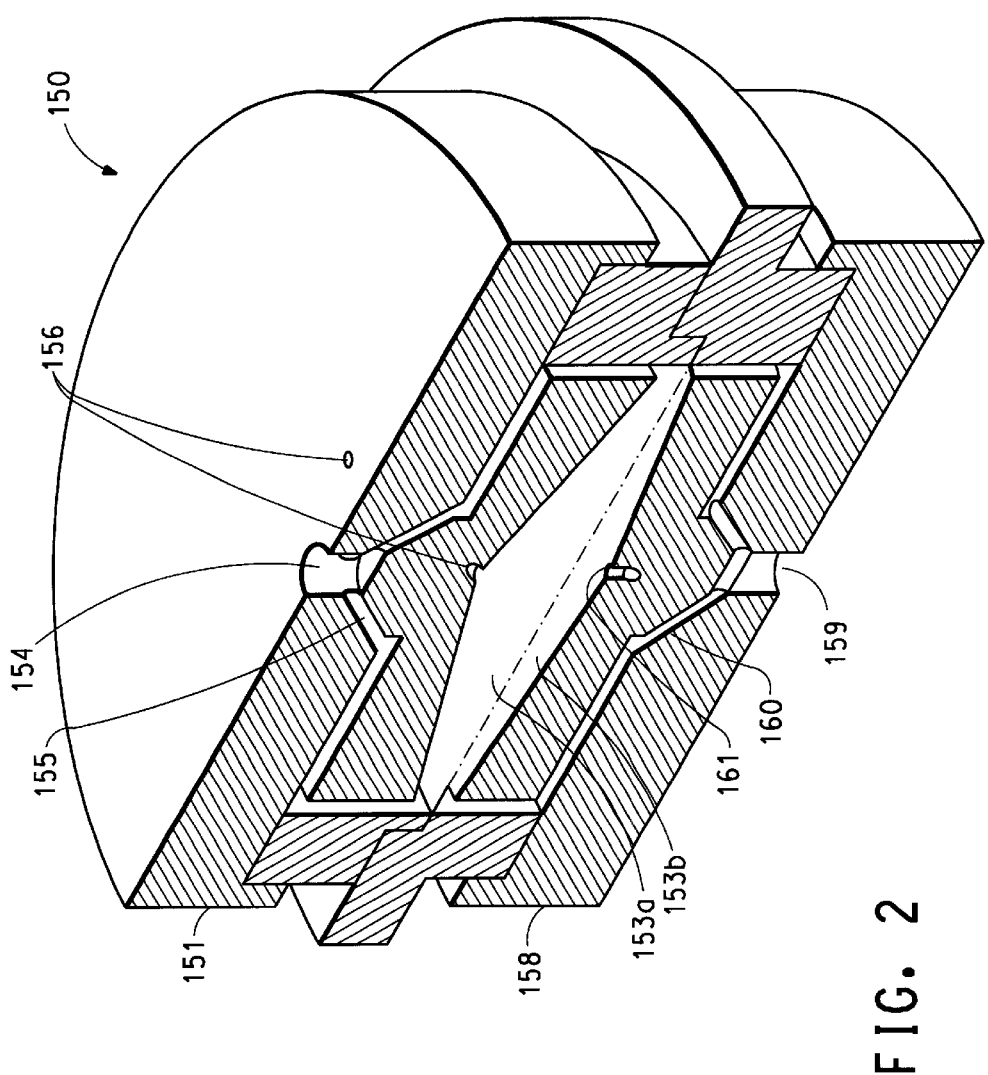
FIG. 2 is a more detailed cross-sectional representation of the sample holder.
Figure 3:
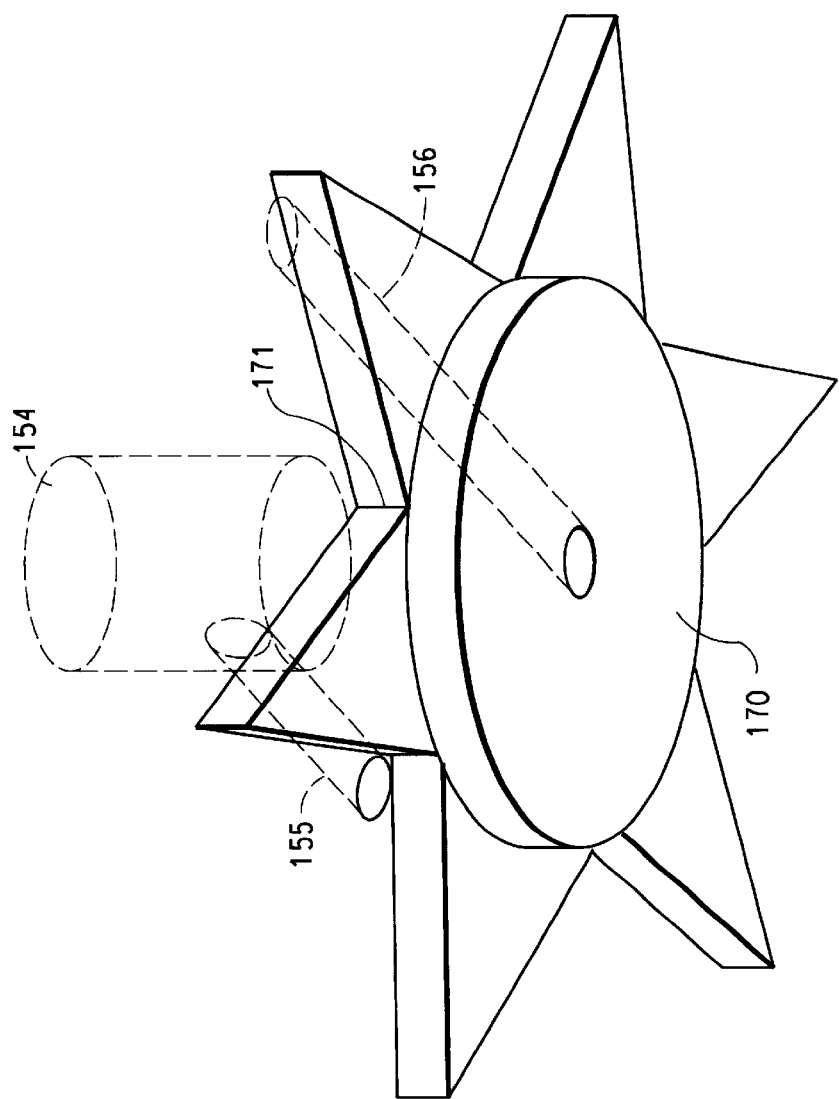
FIG. 3 is a schematic representation of certain internal features of the sample holder.

As shown in FIG. 2, the sample holder comprises an upstream manifold 151 and a downstream manifold 158 that together define an internal chamber 153. Although the terms upstream and downstream are used for convenience, it should be noted here that there is no requirement that the apparatus be oriented as shown in the figures. A sample of the material to be tested can be placed in the holder so that the internal chamber 153 is effectively divided into an upper (upstream) portion 153a and a lower (downstream) portion 153b. The generated challenge particles first enter the upstream manifold 151 through an inlet 154. The flow of challenge particles is divided into a plurality of streams and then conducted to the edges of the sample through passages 155 so that the flow is distributed uniformly across the upstream surface of the test sample. The manifold also contains a star-shaped element 170 as generally depicted in FIG. 3. The star-shaped element is constructed so that the passages 155 extend to the inner apexes 171 of the element. This provides for a uniform outward flow path of the mixture. A significant advantage is that when changing particle sizes during testing, the lack of turbulence allows quicker purging of one particle size, so that there will be no mixing of different particle sizes. Six passages 155 are provided but not all are shown in FIG. 3. However, any number of such passages can be used that provides the advantages noted above. A small fraction (about 300 cubic centimeters) of the challenge particles is extracted from the upper portion 153b through passage 156. The challenge particles are transported to and then counted in the Challenge Condensation Particle Counter (CCPC) 40, which provides continuous monitoring to establish a base line particle count. The CCPC 40 has a small internal pump (not shown) that draws in the mixture.

The downstream manifold 158 is identical in structure to the upstream manifold, except there is a difference in the function. Depending on the barrier property of the sample, some portion of the challenge particles passes through the sample into lower portion 153b. A gas from supply 60 enters manifold 158 through inlet 159 and is distributed through passages 160 to portion 153b. While any gas can be used, air is satisfactory and is of course not expensive as nitrogen, for example, which is used in supply 15. This flow of air is referred to as sweep air because it picks up and transports the challenge particles through passage 161. This leads to FCPC 95, which measures the amount of challenge particles that passed through the sample. As noted above, the manifold 158 is identical to manifold 151, therefore it also contains a structurally identical star-shaped element, but its function is primarily to provide uniform flow of sweep air so that all of the challenge particles are collected. FCPC 95 operates at a constant flow rate of 1.00 l/min using an external vacuum source 100 and an internal critical orifice, which is not shown. When measuring low flow rates, i.e., below 1 l/min, the driving force across the sample is primarily provided by the air demand of FCPC 95 at a constant 1 l/min and is partially provided by HEPA air source 60.

A manometer 55 is connected to sample holder 150 to measure the pressure differential across the sample thereby providing an accurate measure of the flow rate relative to the baseline.

The source 60 that provides air to the downstream side of the sample may be used to adjust the flow of particles in the system. The air passes through HEPA filter 70 before entering the downstream side of holder 150. The term HEPA (High Efficiency Particle Attenuation) means that the air was highly filtered. The HEPA filters 70, 80, 90 keep the air flow throughout the system free of foreign particles that could affect the accuracy. HEPA filters 80, 90 provide vents for excess aerosol to escape or a way for clean air to enter the system as necessary to prevent damage to the instruments. In operation, the particles are delivered to the FCPC 95 within the same time, irrespective of the flow rate through the sample. One advantage of this is allowing for relatively easy development of computer software to automate the testing procedure. It should also be noted that the generator, the monitor, the classifier, the pressure regulator, the manometer, the challenge particle counter, and the filtered particle counter are all adapted for interfacing with a computer for process control and data collection.

There is a pressure regulator 65 in line with the air supply 60 that provides flow control to the system, through an orifice 85. Orifices such as 85 are essentially very small holes, typically 50 to 100 micrometers in diameter, in a sheet of metal, usually brass. They are sized so that at flow rates greater than about 0.5 standard liter per minute, the air flow reaches sonic velocity. This renders the airflow relatively insensitive to fluctuation within the chamber of the sample holder 150 or in other components. This insensitivity allows the flow rate to be kept constant over long periods of time, which is required when adjusting the flow of challenge particles through the sample to near zero by matching the demand of FCPC 95. This flow of sweep air can be varied from 0 to 1.0 l/min., which results in a flow across the sample of 1.0 to 0 l/min., respectively. This shows that the maximum flow through the sample of 1.00 l/min is achieved when the air supply 60 is turned off.

For flow rates of less than 1 l/min, the flow through the sample is the difference in demand between FCPC 95 and the HEPA air supply through critical orifice 85.

There may be excess air that is not required by FCPC 95 and this excess air can be vented through HEPA filter 90 and water trap 92. This can serve as an emergency release to prevent damage to the instrumentation and also provides a visual indication that something may be wrong in the system; a pinched hose, for example.

Figure 4:
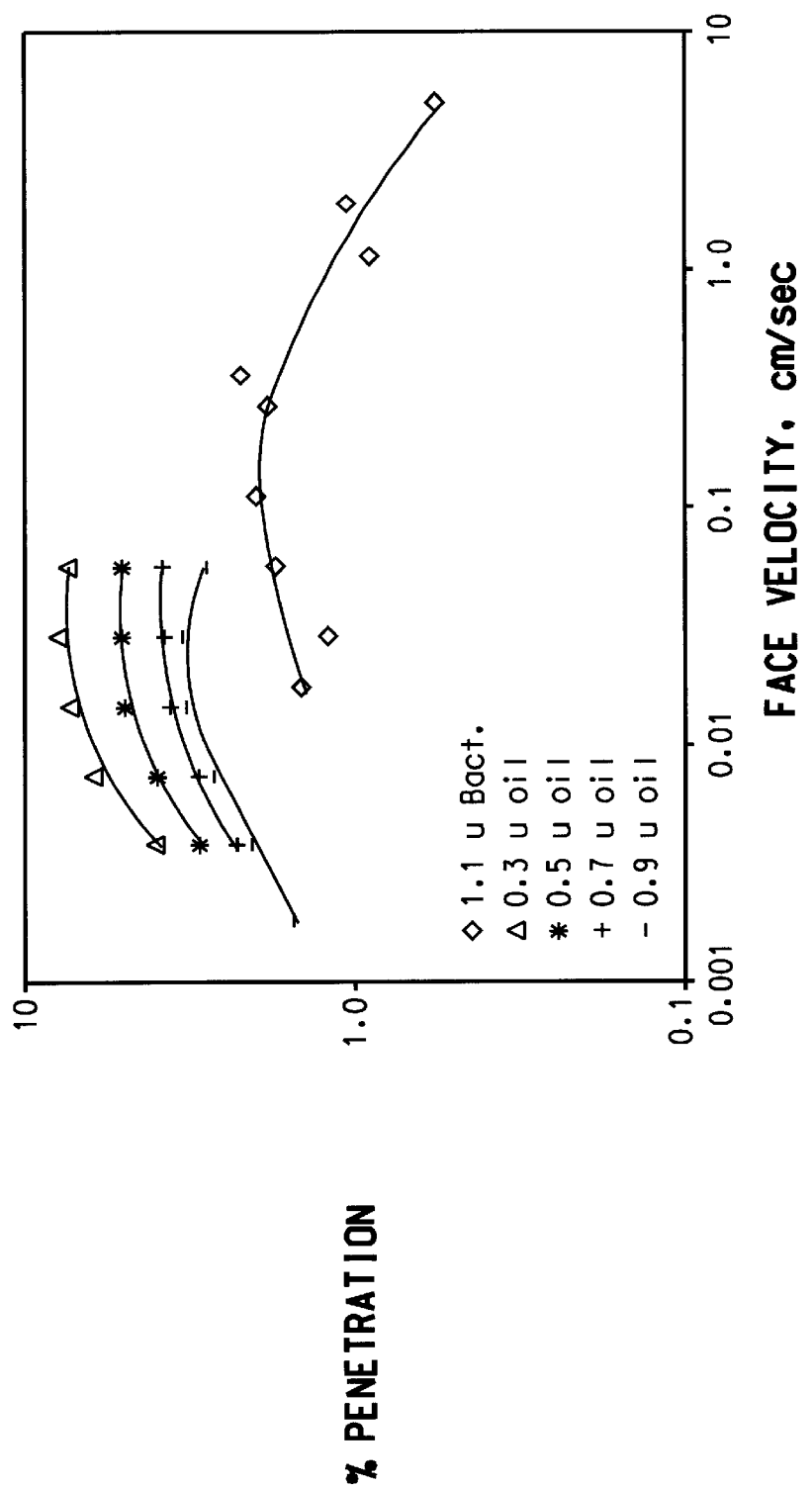
FIG. 4 is a graphical representation comparing the claimed invention and a conventional method.

FIG. 4 shows in graph form that the subject invention provides data at flow rates at least as low as those achieved when microbial agents are used. The graph shows that irrespective of the size of the aerosol oil droplet used in the subject invention the ability to generate data at low flow rates is maintained. As noted above, this limitation of conventional systems is primarily due to their inability to separate flow through the test sample from flow through the particle counter. The ability to separate the flow allows the subject invention to evaluate barrier properties at flow rates approaching zero. This is significant because at higher flow rates the primary mechanism of particle removal is that the particles impact the fibers of the subject material. However, at low flow rates, Brownian movement and electrostatic attraction removes the particles. This phenomenon increases in importance as the residence time of a particle within a material increases.

Figure 5:
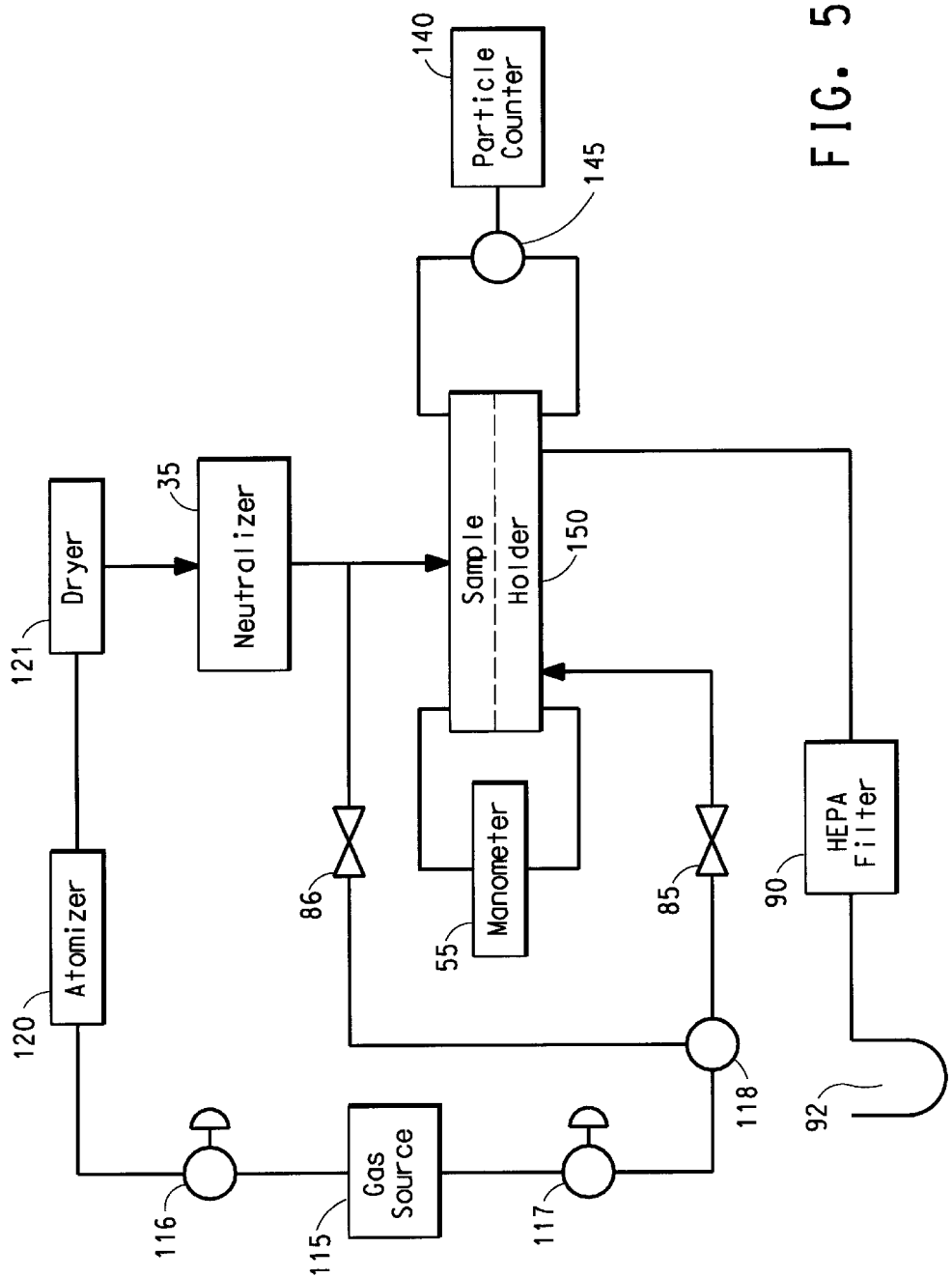
FIG. 5 is a schematic representation of a second embodiment of the apparatus.

An apparatus for a second embodiment of the invention is depicted generally in FIG. 5. Elements that are substantially identical in FIG. 5 and in FIGS. 1–4 have the same character numbers. In this embodiment of the subject invention, instead of the generator system described above, a simpler procedure and apparatus has been devised, wherein an atomizer provides particles of polystyrene latex (PSL) about one micrometer in size, which are introduced into a gaseous medium provided from gas source 115. Preferably, ultra low particulate air (ULPA) is used. The PSL particles are available from Duke Scientific. This provides a simpler system in that it is not necessary to make aerosols that vary in size and therefore a classifier 30 as shown in FIG. 1 is not required. The simpler system can use a dryer 121 to remove moisture from the gas stream. An advantage of the simpler apparatus is that one particle counter 140 can be used, as depicted in FIG. 5. The particle counter uses a valve 145 that switches its input from the challenge particles to the result particles. The result particles are those that passed through the sample material. The challenge is measured before and after each result measurement. The value used in the calculation to characterize the sample material is the average of the two measurements. Although this can introduce some additional error because the particle concentration has some amount of unpredictable variation, it does reduce the cost of the installation significantly. There are other differences in this embodiment that do not significantly change the concept of the invention. For example, orifice 86 is employed to control the flow of air into the sample holder although at somewhat faster speed than that provided by orifice 85. Pressure regulators 116 and 117, as well as selection valve 118 are further used to control air flow through the system.

The subject invention as noted above would be useful in evaluating materials used in barrier or filter applications, such as TYVEK®, a registered trademark of E. I. du Pont de Nemours and Company, Wilmington, Del. (DuPont). Heretofore, the advantages of TYVEK® were not well appreciated because it has an electric charge and electrostatic attraction is an important mechanism at low flow rates. However, the subject invention will be helpful in demonstrating the advantages of TYVEK® in medical products, protective apparel, desiccant packaging, filtration and other applications.

What is claimed is:

1. A method for measuring barrier properties of a material comprising the steps of:
   a) positioning a sample of the material in a holding means comprising a chamber wherein the material divides the chamber into a first portion and a second portion;
   b) providing micrometer-sized particles;
   c) generating a gas for mixing with the particles;
   d) mixing the gas and the particles;
   e) introducing the mixture of the particles and the gas into the first portion and wherein some percentage of the particles pass through the sample from the first portion to the second portion;
   f) extracting from the first portion a small amount of the mixture that does not pass through the sample,
   g) counting the aerosol particles from f) in a particle counter, h) introducing a second gas through a predetermined-sized orifice into the second portion to sweep up particles that have passed through the sample;

i) extracting from the second portion the mixture that passed through the sample, j) counting the aerosol particles from i) in the particle counter, k) comparing the number of particles from g) to the number of particles from j).

2. An apparatus for measuring barrier properties of a sample of material comprising:

a particle atomizer;

means for providing a gas, means for mixing the particles and the gas;

means for transporting the gas and particle mixture;

a sample holder comprising a chamber for positioning the sample wherein the sample divides the chamber into a first portion and a second portion, the first portion having an inlet and at least one outlet, and the second portion having an inlet and at least one outlet, means for introducing a gas into the first portion through the first inlet, means for introducing a gas into the second portion through the second inlet, and wherein the mixture from the mixing means enters the first portion through the first inlet and a first percentage of the aerosol particles exits the first portion through the first outlet into a single counting means and a second percentage of the mixture passes through the material into the second portion and exits the second portion through the second outlet into the single counting means, and means for comparing the particles form the first portion to the number of particles from the second portion.

* * * * *